United States Patent [19]

Fakhri

[11] Patent Number: 5,501,705
[45] Date of Patent: Mar. 26, 1996

[54] METHOD FOR THE TREATMENT OF PSORIASIS WITH ELECTRIC CURRENT

[76] Inventor: Omar Fakhri, 115 Broadley Street, London NW8, United Kingdom

[21] Appl. No.: 989,815

[22] Filed: Dec. 9, 1992

Related U.S. Application Data

[63] Continuation of Ser. No. 679,000, Jun. 13, 1991, abandoned.

[30] Foreign Application Priority Data

Oct. 31, 1988 [GB] United Kingdom .................. 8825464
Dec. 29, 1988 [GB] United Kingdom .................. 8830318

[51] Int. Cl.⁶ ................................................. A61N 1/20
[52] U.S. Cl. ........................................... 607/75; 607/149
[58] Field of Search ..................... 128/796, 797, 128/799, 802, 419 R, 381, 382, 377, 378; 607/2, 75, 148, 149

[56] References Cited

U.S. PATENT DOCUMENTS

| 171,934 | 1/1876 | Hathaway | 128/796 X |
|---|---|---|---|
| 238,721 | 3/1881 | Sharp | 128/799 X |
| 399,084 | 3/1889 | Schmalz et al. | 128/796 |
| 1,123,683 | 1/1915 | Clague | 128/796 X |
| 3,762,396 | 10/1973 | Ballentine et al. | 128/791 X |
| 4,398,545 | 8/1983 | Wilson | 128/803 X |

FOREIGN PATENT DOCUMENTS 3702264 7/1987 Germany ................................ 128/796

OTHER PUBLICATIONS

Fakhri et al, "The Effect . . . Skin Burns", JBCR, vol. 8, No. 1, Jan.–Feb. 1987, pp. 15–18.

Primary Examiner—Lee S. Cohen

[57] ABSTRACT

The invention provides electro-therapy apparatus which can be readily attached to the patient and which is arranged to pass current through the patient by way of the arms and legs. The electric current is supplied by way of a low voltage source and the apparatus is particularly useful in treating various dermatological and rheumatological diseases, and diseases resulting from impaired peripheral circulation and oedema.

3 Claims, 3 Drawing Sheets

5,501,705

METHOD FOR THE TREATMENT OF PSORIASIS WITH ELECTRIC CURRENT

This application is a continuation of application Ser. No. 07/679,000, filed Jun. 13, 1991, now abandoned.

TECHNICAL FIELD

The invention relates to an apparatus and method for treating the human body by way of electric stimulation.

DISCLOSURE OF THE INVENTION

The invention seeks to provide such apparatus which is simple to couple to the body and simple to operate.

According to one aspect of the present invention there is provided apparatus for treating the human body by way of electric stimulation, the apparatus comprising first electrode means shaped to provide a substantial area of engagement by the human hands, second electrode means shaped to provide a substantial area of engagement by the human feet, and an electrical supply means connectable with the first and second means so as to thereby pass current through the body.

Preferably, the apparatus is provided in the form of a chair for supporting the patient, the arm and foot rests of which chair are provided with the electrode means. Advantageously, the electrode means provided on the chair arms each comprise a plurality of grooves for receiving the patient's fingers.

Alternatively, the invention may be provided in portable form. As such, the electrode means for providing a substantial area of engagement by the human hands may be provided on a unit which can be placed on the patient's lap during treatment. Also, the electrode means for providing a substantial area of engagement by the human feet may be provided on a unit which can be placed on the floor. A separate portable power source for connection to the lap and floor units is also provided which may comprise an a.c. mains transformer and rectification circuitry or a battery. Control means can be provided on the lap unit and/or in the power source.

Accordingly, the portable apparatus can be readily set up in a domestic location with the patient sitting in a typical household chair. The electrode means are respectively placed on the floor and on the patient's lap so that electrical contact to the hands and feet can be made and the treatment commenced.

According to another aspect of the present invention there is provided a method for treating dermatological and rheumatological diseases of auto-immune origin, the method comprising passing a d.c. electric current through the human body.

According to yet another aspect of the present invention, there is provided a method for treating inflammatory diseases of the skin and diseases resulting from impaired peripheral circulation and oedema, the method comprising passing a d.c. electric current through the human body.

Although the invention is not to be regarded as dependent in any way on these explanations, it is thought that, in respect of diseases of auto-immune origin, the passage of the electric current interferes with the auto-immune reaction, and in respect of diseases associated with circulation difficulties, that the current increases peripheral circulation by stimulating the release of the calcitonic gene related peptide (CGRO), a potent vasodilator, and by increasing tissue permeability.

Preferably, the current is passed between the patient's hands and feet.

BRIEF DESCRIPTION OF THE DRAWINGS

The invention is described further hereinafter, by way of example only, with reference to the accompanying drawings in which.

BEST MODE OF CARRYING OUT THE INVENTION

Figure 1:
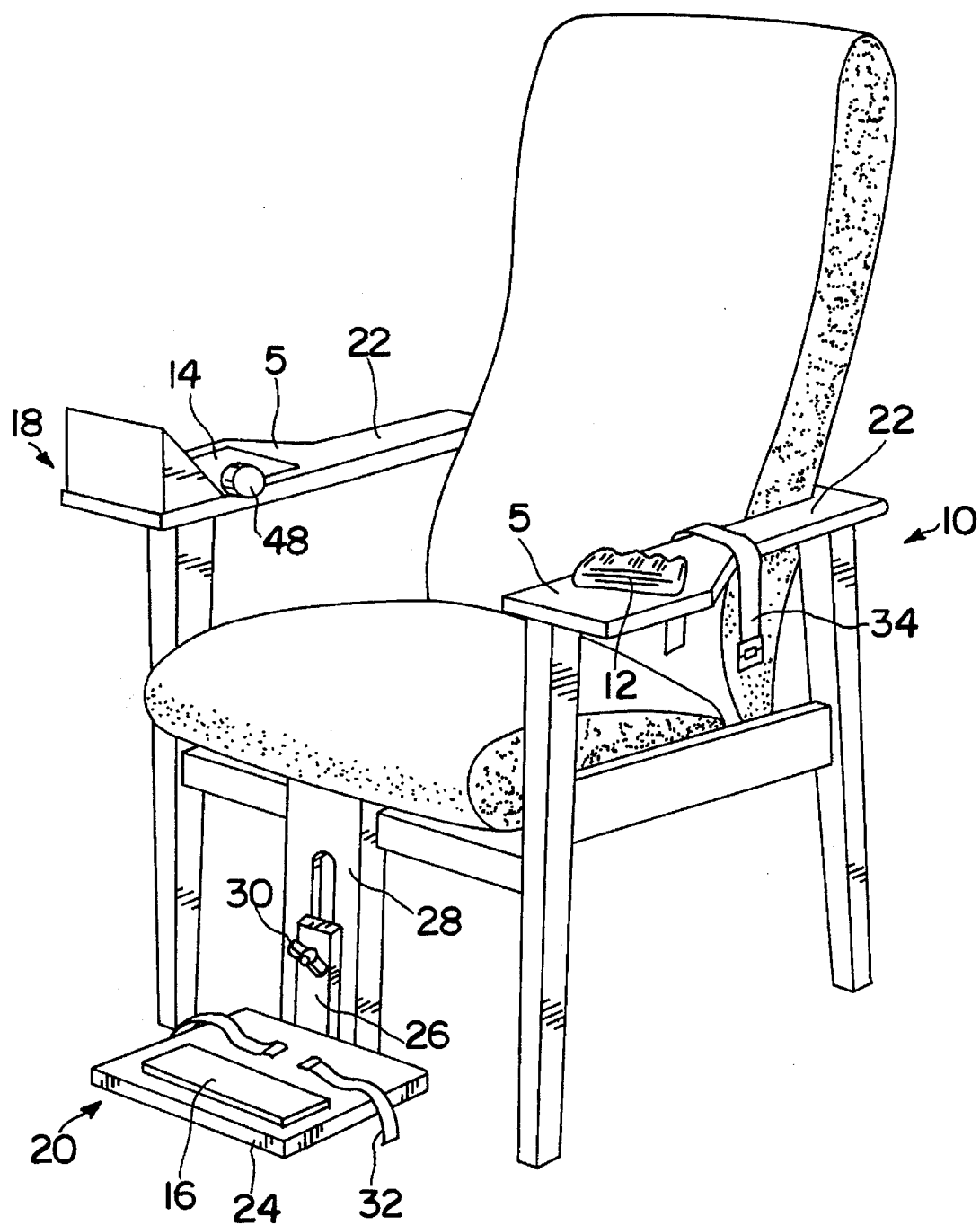
FIG. 1 illustrates apparatus in the form of an electrotherapy chair according to the present invention.

The apparatus of the present invention comprises a chair 10 fitted with electrodes 12, 14, 16 to be contacted by the patient and electrical source and control means 18 for supplying appropriate voltages to the electrodes 12, 14, 16.

The apparatus of the invention is designed to conform to the British Standard for the safety of medical electrical equipment B.S. 5724.

The power unit receives current from a mains (240 V AC.) source and rectifies it so as to provide a variable voltage direct current. The adjustable d.c. voltage may be of the order 0–36 V and provides an adjustable d.c. current of magnitude 0–50 mamp.

The chair 10 can comprise a typical easy chair with a wooden frame on which are mounted upholstered seat and back rest portions for comfortable supporting the patient when receiving treatment. The chair is fitted with a foot rest 20 and with arm rests 22 having enlarged support areas 5 at their free ends.

The foot rest 20 comprises a base plate 24 extending generally horizontally from an upright 26 slidable vertically on a support 28 extending downwardly from the chair frame. A screw clamp 30 permits the distance of the base plate 24 from the floor to be adjusted to accommodate the patient's legs comfortably during treatment. The base plate 24 is provided with an electrode 16 formed of a stainless steel plate. The rear part of the foot rest is provided with an elastic strap 32 for engaging the patient's feet or ankles so as to prevent reflex movements of the feet and legs during treatment.

The front region of the arms 22 of the chair 10 are formed so as to be suitable to serve as rests for the palm of the patient's hands.

The arm rest for the patient's left arm is fitted with a stainless steel electrode 12 comprising four grooves for receiving the fingers of the patient's left hand and means for restraining reflex movement of the patient's hand and arm which conveniently comprise an elastic strap 34. Instead, one or more clips can be employed. The clip or clips or a strap with a buckle or other releasable fastener having resilient links between which the wrist or lower arm can be placed.

The arm rest 22 for the patient's right arm comprises two main features, namely a grooved stainless steel electrode 14 and on-off rheostat switch for current control, and a display unit 18.

Figure 2:
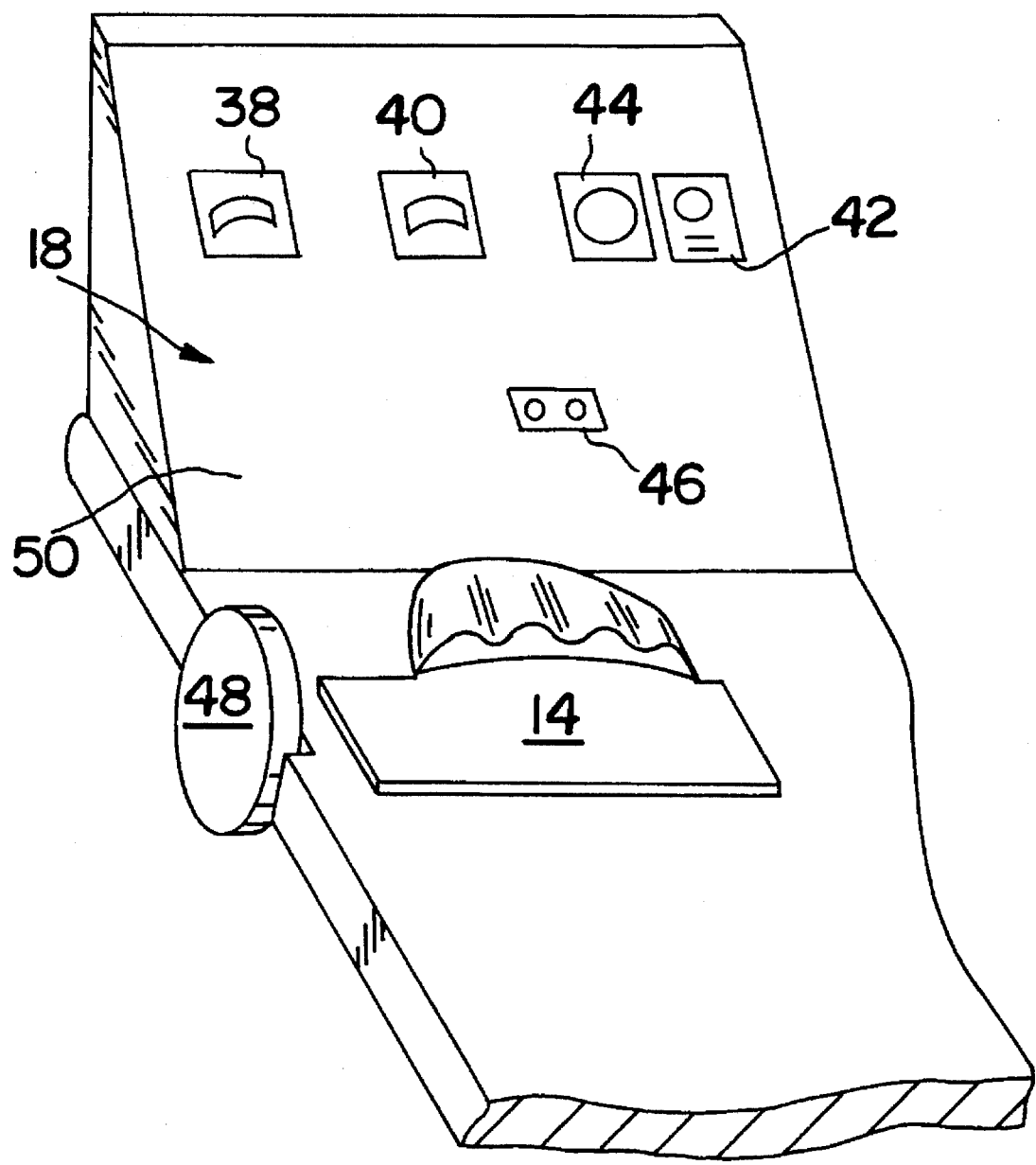
FIG. 2 illustrates the current control panel of the apparatus of FIG. 1.

The display unit 18 is illustrated further in FIG. 2 and includes a voltmeter 38, an ammeter 40, a pre-set timer 42, a time lapse digital timer 44 and a device 46 for emitting an audio signal on completion of the treatment.

The right arm rest includes a grooved stainless steel electrode 14 and an on-off rheostat switch 48 which can be operated by the patient's thumb. The display unit panel 50 comprising a voltmeter, ammeter and timer displays, is disposed at an angle of 45° to the surface of the arm rest so that it is comfortably visible by the sitting patient.

The electrodes 12, 14, 16 are connected to a power pack (not shown) which is located under the chair. The power pack receives an alternating current from the mains supply and rectifies it to a low voltage direct current supply, typically of magnitude 0–36 V and 0–50 mamp. Alternatively, a battery can be used as the power supply. The two hand electrodes 12, 14 are connected in parallel and comprise the anode and the foot electrode 16 comprises the cathode.

The passage of the current through the body is beneficial in treating various inflammatory diseases of the skin and those of auto-immune origin such as psoriasis, certain types of allergic reactions and various rheumatological diseases such as rheumatoid arthritis and diseases resulting from impaired peripheral circulation and oedema such as varicose skin ulcers. The chair 10 is particularly designed to facilitate the advantageous passage of the current through the whole body from the forefinger to the toes.

During treatment, the patient sits on the chair, rests his feet on the foot rest so that the toes and the front part of the feet rest on the stainless steel plate electrode 16. The feet are then retained on the foot rest 20 by the elastic strap 32, or other fastener means.

The patient's left hand is located in position with the fingers received in the grooves of the electrode 12 and the lower portion of the left arm is wrapped with the elastic strap 34, or received in the clip means, to prevent reflex movement thereof.

The patient's right arm is located in position with the fingers received in the grooves of the electrode 14. The pre-set timer 42 is set to the desired time. The rheostat switch 48 is turned to the "on" position and is gradually adjusted by the patient's thumb so as to increase the supplied current and until the patient feels a tingling sensation without discomfort.

The treatment continues until the time period expires, which is indicated by an alarm signal from the alarm device 46. On completion of the treatment period, a current control device initiates a controlled reduction in the magnitude of the current until current flow is terminated. Typically, the duration of the treatment period for each session is in the range 30–60 minutes and depends on the severity of the condition.

Alternatively, the lapsed treatment time can be viewed on the display 18 and the patient can re-adjust or terminate the current to suit his comfort at any time during the treatment. The rheostat switch 48 allows the current to be increased or decreased gradually so as to avoid discomfort for the patient.

The treatment sessions are repeated twice a week until complete remission from the disease is achieved. In the case of diseases of auto-immune origin such as psoriasis and rheumatoid arthritis, the treatment session should be provided after remission is achieved at a lower rate (once a week for four to six weeks) then decreased further to once every two weeks and continued thereafter at this rate to avoid relapse.

Conduction of the electric current from the electrodes to the body can be better facilitated by use of a conductive gel. Thus, a suitable gel can be applied to the contact surfaces of the electrodes 12, 14, 16.

Figure 3:
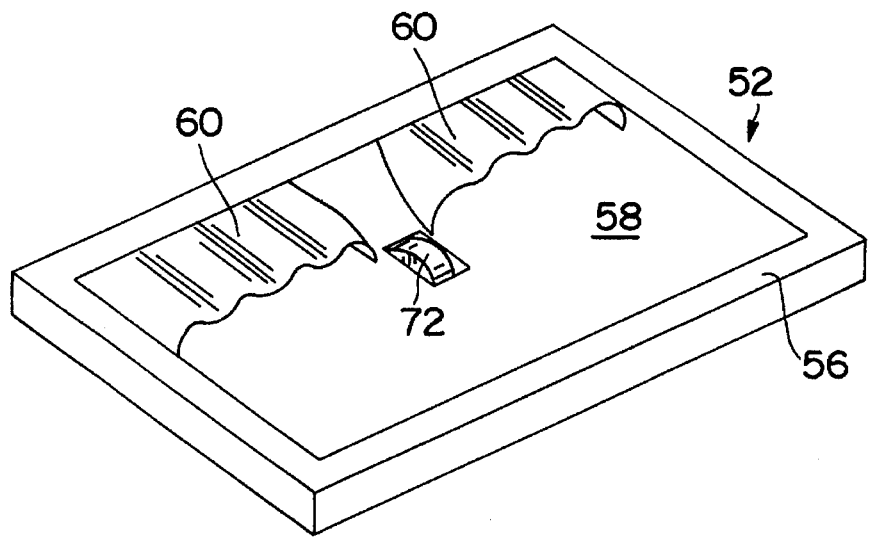
FIGS. 3 and 4 illustrate alternative embodiments of the electrode means of the apparatus according to the present invention.
Figure 4:
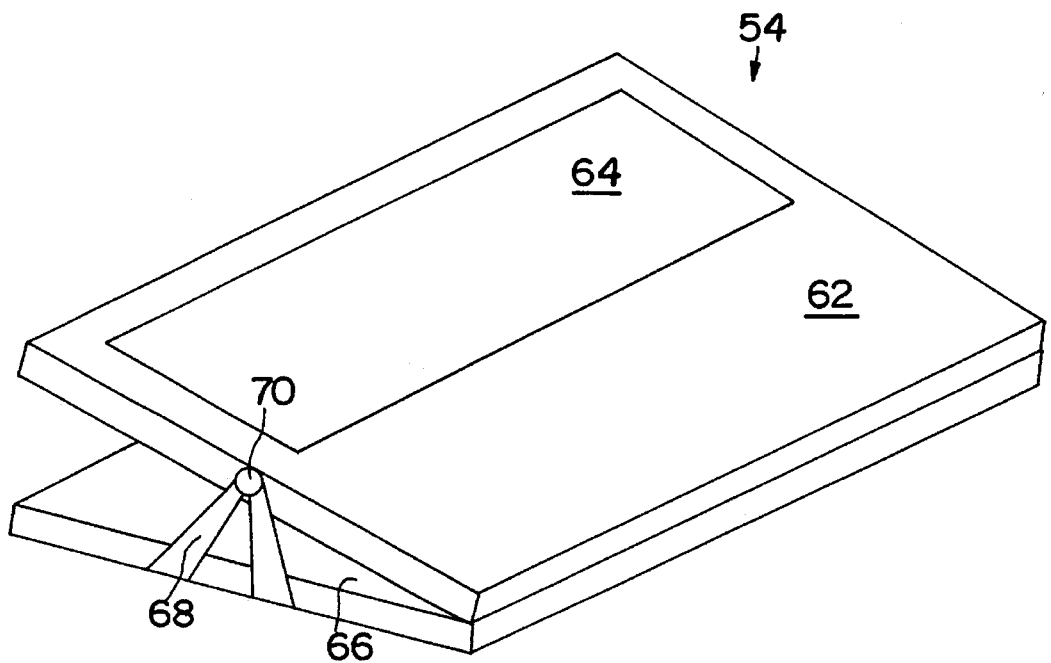

FIGS. 3 and 4 illustrate alternative embodiments of the electrode means 52, 54 of the portable apparatus according to the invention.

The apparatus provides for reception on the patient's lap a unit 52 comprising an insulating base board 56 mounting a single electrode means 58 for engagement by the patient's hands and which includes a plurality of grooves 60 for receiving the patient's fingers. An aperture is provided in the electrode, through which extends an on/off rheostat switch 72 for controlling the magnitude of the current as described above.

The apparatus also includes electrode means 54 provided with a single electrode 64 for engagement by the front part of the patient's feet. The electrode 64 is mounted on an insulator board 62. A spindle 70 is located along the central longitudinal axis of the board and pivotally engages with supports 68 (only one of which is shown in FIG. 3) extending from a base plate 66. As such, the patient's feet are located on the board 62 and electrode 64 of the electrode means 54. The patient can then cause the board 62 to pivot into the most comfortable position for receiving the feet.

The portable apparatus also includes a portable power source (not shown) for connection by suitable leads to the lap and/or floor units either permanently or releasably by suitable plug or socket connectors. The apparatus is also advantageously provided with the control and timer apparatus described above with reference to FIGS. 1 and 2. In this case the control and timer apparatus is associated with the portable power source.

The aim of the apparatus of the invention is to pass the current safely and comfortably throughout the whole body from the forefingers to the toes and the use of electric stimulation in the form described, to treat dermatological and rheumatological diseases resulting from inflammation, those of auto-immune origin and diseases resulting from impaired peripheral circulation and oedema, provides a novel treatment for such diseases.

I claim:

1. A method of treatment of psoriasis in humans, comprising passing D.C. electric current through the body of a patient suffering from psoriasis, from the fingertips to the toes, and gradually increasing the electric current to a predetermined level.

2. A method as claimed in claim 1, wherein said predetermined level does not exceed 36 volts.

3. A method as claimed in claim 1, wherein said predetermined level is that at which the patient feels a tingling sensation without discomfort.

* * * * *